United States Patent [19]

Brannon et al.

[11] 4,082,754
[45] Apr. 4, 1978

[54] DES-N-METHYLVINDOLINE

[75] Inventors: Donald R. Brannon, Pittsboro; Norbert Neuss, Indianapolis, both of Ind.

[73] Assignee: Eli Lilly and Company, Indianapolis, Ind.

[21] Appl. No.: 637,908

[22] Filed: Dec. 4, 1975

Related U.S. Application Data

[62] Division of Ser. No. 398,724, Sep. 19, 1973, Pat. No. 3,989,593.

[51] Int. Cl.$^2$ ............................................. C07D 401/02
[52] U.S. Cl. ................................. 260/287 P; 195/29
[58] Field of Search .................... 260/293.53, 287 P

[56] References Cited

U.S. PATENT DOCUMENTS

| | | | |
|---|---|---|---|
| 3,354,163 | 11/1967 | Gorman | 260/287 |
| 3,422,112 | 1/1969 | Gorman et al. | 260/287 |
| 3,899,493 | 8/1975 | Jovanovics et al. | 260/287 P |
| 3,989,593 | 11/1976 | Brannon et al. | 195/29 |

FOREIGN PATENT DOCUMENTS

| | | | |
|---|---|---|---|
| 728,535 | 11/1972 | South Africa | 260/287 P |

OTHER PUBLICATIONS

Neuss et al., Helv. Chim. Acta., vol. 57, pp. 1886–1893 (1974).

Gorman et al., J. Am. Chem. Soc., vol. 84, pp. 1058–1059 (1962).

*Primary Examiner*—Henry R. Jiles
*Assistant Examiner*—Richard A. Schwartz
*Attorney, Agent, or Firm*—James L. Rowe; Everet F. Smith

[57] ABSTRACT

Vindoline and vinblastine demethylated by submerged culture fermentation with *S. albogriseolus*.

1 Claim, No Drawings

DES-N-METHYLVINDOLINE

CROSS REFERENCE

This application is a division of our copending application Ser. No. 398,724, filed 9/19/73 now U.S. Pat. No. 3,989,593.

BACKGROUND OF THE INVENTION

Several naturally-occurring dimeric alkaloids obtainable from *Vinca rosea* have been found active in the treatment of experimental malignancies in animals. Among these are leurosine (U.S. Pat. No. 3,370,057), vincaleukoblastine (vinblastine or VLB) (U.S. Pat. No. 3,097,137), leurosidine (vinrosidine) and leurocristine (VCR or vincristine) (both in U.S. Pat. No. 3,205,220). Two of these alkaloids, VLB and vincristine, are now marketed as drugs for the treatment of malignancies, particularly the leukemias and related diseases in humans. Vinblastine and vincristine can be represented by Formula I below which also illustrates the conventual numbering system for the dimeric indole alkaloids.

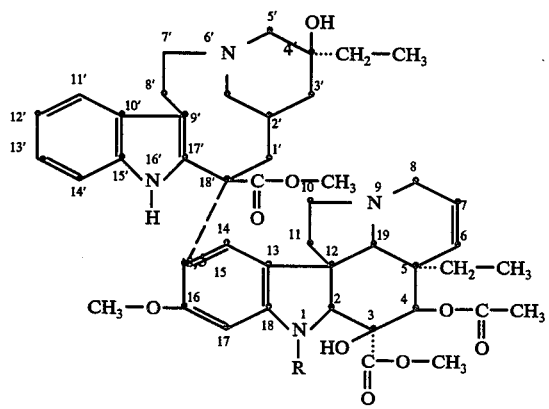

When R is methyl in Formula I, the compound is vinblastine and when R is formyl, the compound is vincristine.

In the Formula I compounds, the lower ring is usually referred to as the vindoline moiety, in that vinblastine is a 15-substituted vindoline and vincristine is a 15-substituted derivative of a modified (1-formyl rather than 1-methyl) vindoline. N-desmethylvinblastine (1-desmethylvinblastine) or desformylvincristine is also a 15-substituted modified vindoline. The compound is described in U.S. Pat. No. 3,354,163.

U.S. Pat. No. 3,422,112 describes the preparation of 15-substituted vindolines by the reaction of vindoline with various indole derivatives including perivinol, 18-hydroxy dihydrocleavamine, 18-hydroxyibogamine, vobasinol and the like.

The fermentation of vindoline with S. albogriseolus to produce other metabolites has been reported by Mallet et al. in the abstracts of the 151st meeting of the American Chemical Society fall 1967 at Pittsburgh, Pa.

N-desmethyl (1-desmethyl) vindoline has not hitherto been described.

SUMMARY OF THE INVENTION

This invention provides a process for N-demethylating indole alkaloids which comprises subjecting a compound of Formula II

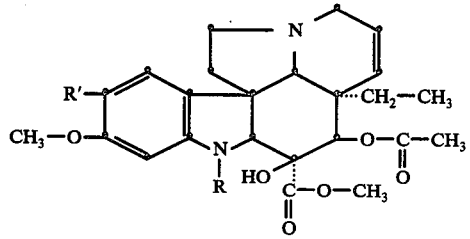

wherein R is methyl and R¹ is hydrogen or the radical

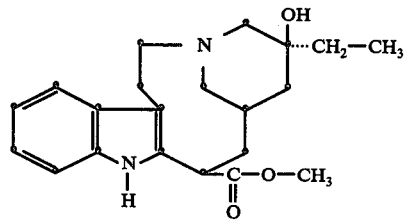

to a submerged culture fermentation of the microorganism S. albogriseolus (A17178) to produce an N-demethylated compound according to Formula II above in which R is hydrogen and R¹ has the same meaning as before.

The organism *S-albogriseolus* (A17178) is deposited with the Northern Regional Research Laboratory, Peoria, Illinois, with the number NRLL 5748. The organism is fully described in *Antibiotics and Chemotherapy*, 4, 653–6 (1954) and in *Int. J. Syst. Bact.*, 18, 279–392 (1968).

In the above Formula II when R¹ is hydrogen, the compound is denominated vindoline and when R¹ is the complex indole radical (a cleavamine derivative), the compound is denominated vinblastine.

In carrying out our novel fermentation, an *S. albogriseolus* culture is innoculated into a vegetative corn-steep soy medium where it is incubated on a rotary shaker 30° C. for from 2 to 3 days. At the end of this time, an 8 percent innoculum of the culture is transferred to a series of flasks containing a peptone-amine medium and the culture is grown in this medium on a rotary shaker at 30° C. for about 24 hours. At this point in time, vindoline or vinblastine is added to the culture medium usually as a 1 to 1 acetone:water solution containing about 50 mg. of the alkaloid for each 2 ml. of solvent. Each flask contains about 150 ml. of medium and the alkaloid is added so as to provide 50 milligrams per 150 ml. of medium. The fermentation is carried out for from 5 to 6 days with shaking at about 30° C. The culture is then harvested by acidifying, filtering, basifying to a pH in the range 9–10 and then extracting the alkaloidal material which is insoluble in the alkaline medium with a water-immiscible solvent such as methylenedichloride or the like. The residual alkaloidal material obtained by evaporation of the extracting solvent is then separated into its components by a gradient pH separation procedure, by high-pressure chromatography over alumina or by other procedure available for separating closely related indole alkaloids. Other products produced in the fermentation with *S. albogriseolus* using vindoline as a substrate are disclosed in Mallet et al. (loc. cit.).

In carrying out our novel fermentation, *S. albogriseolus* (S17178) or a morphological variant thereof is employed. As previously mentioned this strain has been desposited to the Northern Regional Research Laboratory, Peoria, Illinois where it has been given the index NRRL 5748. As would be apparent to those skilled in the art, other related organisms as distinguished from morphological variants of *S. albogriseolus,* are capable of demethylating vindoline or vinblastine in a submerged culture fermentation.

This invention is further illustrated by the following specific examples:

EXAMPLE 1

Des-N-methylvindoline

*S. albogriseolus* (A17178.5) was grown on a cornsteep soy slant (CSS XII) having the following composition cerelose, 15 g.; soybean meal (nutrisoy grits), 15 g.; corn-steep solids (50 percent solids), 8 ml.; NaCl, 5 g.; CaCo$_3$, 2 g.; tap water to 1 l. The pH of the medium was adjusted to 6.0, and the medium sterilized by autoclaving for 25 minutes. The growth of *S. albogriseolus* thus obtained was transferred from the CSS XII slants to a vegetative medium containing 100 ml. of CSS XII medium per 500 ml. flask. The vegetative culture was incubated at 30° C. while being shaken on a rotary shaker at 250 rpm. After 72 hours, an 8 percent inoculum of *S. albogriseoulus* thus prepared was transferred to 500 ml. Erlenmeyer flasks each containing 150 ml. of PNZ medium having the following ingredients: cerelose, 25 g.; soluble starch, 10 g.; peptone, 40 g.; NZ amine A, 4 g.; MgSO$_4$·7H$_2$O, 5 g.; blackstrap molasses, 5 g.; CaCO$_3$, 2 g.; tap water to 1 l. The pH of this medium was adjusted to 7.6 and the medium autoclaved for 25 minutes before use. The PNZ inoculated medium was incubated at 30° C. on a rotary shaker at 250 rpm. After 24 hours of growth, vindoline was added at the rate of 50 mg. per flask as a solution in 2 ml of a 1 to 1 acetone-water mixture. The fermentation was continued for 5 days at the end of which time it was harvested by adjusting the pH of the medium to 3.4 and then filtering. The pH of the medium was next adjusted to a pH in the range 9-10 and the base-insoluble materials, chiefly vindoline and vindoline fermentation products, were extracted therefrom with methylenedichloride. The methylene dichloride extract was dried, and the methylenedichloride removed therefrom in vacuo. The residual alkaloids were then further purified as follows: two g. of the alkaloidal extract were dissolved in benzene and the benzene solution chromatographed over 100 g. of silica in a 1.25 inch column. The chromatogram was developed with 1.5 l. of benzene, 2 l. of a benzeneethyl acetate (95:5) mixture, 400 ml. of a benzene-ethyl acetate (3:1) mixture and finally with 1 l. of a benzeneethyl acetate (1 to 1) solvent. Further elution with 1 l. of the last solvent mixture gave four fractions containing, totally, 95 mg. of des-N-methylvindoline melting at about 102° to 104° C. The product had a typical NH band at 3420 cm.$^{-1}$ not present in vindoline itself. NMR spectrum was characterized by a lack of N—CH$_3$ protons at δ2.68 ppm and by the appearance of two new peaks at δ4.50 ppm (NH doublet) and δ4.15 ppm (C-2 proton doublet). The remainder of the NMR spectrum was as expected, being similar in appearance and in chemical shifts to the vindoline spectrum. The structure of the compound was also confirmed by mass spectroscopy which gave the predicted molecular weight and a fragmentation pattern typical for compounds of this type.

EXAMPLE 2

Des-N-methylvinblastine

The fermentation was carried out in similar fashion to that of example 1 except that vinblastine rather than vindoline was added at the rate of 50 mg. per 150 ml. of NPZ medium and the fermentation was carried out for 6 days rather than 5. At the end of the fermentation, 3 l. of fermentation broth were acidified with 10 percent aqueous hydrochloric acid to pH = 4.6. The acidic broth was filtered and then extracted with two to one liter portions of methylenedichloride. The methylenedichloride extracts were combined and dried, and the methylenedichloride removed therefrom by evaporation in vacuo to yield a residue weighing about 537 mg. The residue was subjected to a pH gradient extraction procedure by dissolving the residue in 50 ml. of 0.1 M citric acid at pH = 2.3. This solution was extracted with two-25 ml. portions of methylenedichloride and the methylenedichloride extracts were combined. The pH of the solution was then raised to pH = 3.0 and the extraction repeated and so on up through pH = 5.0. The Table I below gives the results of this gradient pH extraction procedure.

Table I

|    | pH  | residue in mg. |
|----|-----|----------------|
| A. | 2.3 | 230 mg.        |
| B. | 3.0 | 87             |
| C. | 3.5 | 60             |
| D. | 4.0 | 25             |
| E. | 4.5 | 12             |
| F. | 5.0 | 9              |

Fractions "D" and "E" were shown to contain des-N-methylvinblastine both by thin layer of chromatography in two dimensions and by high pressure liquid chromatography over alumina. des-N-methylvinblastine thus obtained was shown to be identical in behavior with authentic des-N-methylvinblastine prepared by the procedure of U.S. Patent 3,354,163. des-N-methylvinblastine can also be isolated from the mixed alkaloid fermentation product by chromatography, particularly high pressure liquid chromatography.

We claim:
1. Des-N-methylvindoline.

* * * * *